United States Patent [19]

Reiffenrath et al.

[11] Patent Number: 5,087,764
[45] Date of Patent: Feb. 11, 1992

[54] PROCESS FOR THE PREPARATION OF 2,3-DIFLUOROBENZENES

[75] Inventors: Volker Reiffenrath, Rossdorf; Joachim Krause, Dieburg, both of Fed. Rep. of Germany

[73] Assignee: Merck Patent Gesellschaft mit beschränkter Hafung, Darmstadt, Fed. Rep. of Germany

[21] Appl. No.: 359,667

[22] PCT Filed: Feb. 27, 1989

[86] PCT No.: PCT/EP89/00181
§ 371 Date: May 12, 1989
§ 102(e) Date: May 12, 1989

[87] PCT Pub. No.: WO89/08629
PCT Pub. Date: Sep. 21, 1989

[30] Foreign Application Priority Data

Mar. 10, 1988 [DE] Fed. Rep. of Germany ....... 3807910

[51] Int. Cl.$^5$ .............................................. C07C 25/13
[52] U.S. Cl. .................................... 568/656; 568/775; 568/661; 570/127; 570/128; 570/129; 562/474; 562/469; 558/425; 546/346; 546/339
[58] Field of Search ............................... 568/656, 775

[56] References Cited

U.S. PATENT DOCUMENTS 4,366,330 12/1982 Gray et al. ........................... 568/775
4,429,153 1/1984 Punja ................................... 568/656

Primary Examiner—Robert T. Bond
Attorney, Agent, or Firm—Millen, White & Zelano

[57] ABSTRACT 1,4-disubstituted 2,3-difluorobenzenes according to formula I are suitable as intermediates for the synthesis of liquid crystalline compounds.

15 Claims, No Drawings

PROCESS FOR THE PREPARATION OF 2,3-DIFLUOROBENZENES

The invention relates to a process for the preparation of 1,4-disubstituted 2,3-difluorobenzenes, in which 1-substituted 2,3-difluorobenzenes are deprotonated in the 4-position using an organometallic reagent and optionally reacted with an electrophile. The invention additionally relates to 1,4-disubstituted 2,3-difluorobenzenes, in particular those which are prepared according to the abovementioned process. Excluded from the invention are fluorinated oligophenyls of the formula T

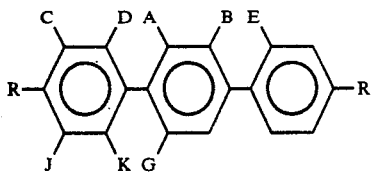

wherein
the terminal substituents
R and R' are in each case independently of one another alkyl or alkenyl radicals having up to 15 C atoms optionally substituted by CN or by at least one halogen atom, wherein one or more non-adjacent CH$_2$ groups of these radicals may also be replaced by —O—, —S—, —CO—, —O—CO—, —CO—O—, —O—CO—O— or —C≡C—, one of these radicals R is also a group of the formula

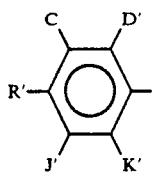

with one of the following pairs of lateral substituents both substituents are fluorine: (A, B), (C, D), (C', D') and all other lateral substituents are hydrogen or fluorine.

These compounds are the subject of the undisclosed Patent Applications P 3,807,956, P 3,807,862, GB 8,806,220 and WO 87-00515.

In preparative organic chemistry, processes for the metalation of aromatics are of increasing importance. It has been shown that in substituted aromatics regioselective metalations are possible for reasons of orientation effects. Thus, for example, 1,2- and 1,3-difluorobenzene can in each case be metalated regiospecifically in the ortho-position to give 2,3- or 2,6-difluorophenyllithium.

The lithiated compounds are stable below −50° C. and represent useful intermediates in the synthesis of many difluoroaromatics (A.M. Roe, Chem. Comm. 22, 582, 1965).

It has now surprisingly been found that 2,3-difluorobenzenes suitably substituted in the 1-position can be selectively metalated in the 4-position. 1,4-disubstituted 2,3-difluorobenzenes can thus be prepared either by deprotonating 2,3-difluorobenzenes substituted in the 1-position with an organometallic reagent and optionally reacting with an electrophile or, starting from 1,2-difluorobenzene, initially deprotonating in the one ortho-position, as described above, then reacting with an electrophile and subsequently repeating the process in the second ortho-position (ortho to F) with a second equivalent of base and, if desired, an electrophile.

The compounds obtainable by these processes are, depending on substitution, useful intermediates in the synthesis of liquid crystalline compounds or compounds which, as components of liquid crystalline phases, improve the dielectric anisotropy or other parameters of the latter. However, they are very generally of interest as intermediates in industrial organic chemistry.

The invention therefore relates to a process for the preparation of 1,4-disubstituted 2,3-difluorobenzenes, excluding fluorinated oligophenyls of the formula T

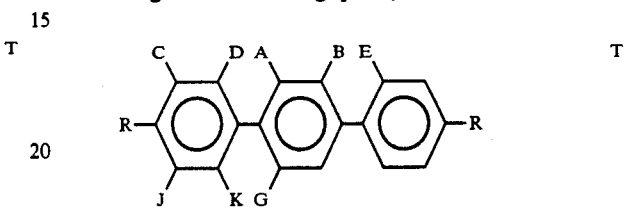

wheein
the terminal substituents
R and R' are in each case independently of one another alkyl or alkenyl radicals having up to 15 C atoms optionally substituted by CN or by at least one halogen atom, wherein one or more non-adjacent CH2 groups of these radicals may be replaced by —O—, —S—, —CO—, —O—CO—, —CO—O—, —O—CO—O— or —C≡C—, one of these radicals R is also a group of the formula

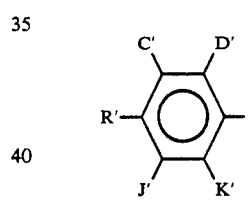

with one of the following pairs of lateral substituents both substituents are fluorine: (A, B), (C, D), C', D) and all other lateral substituents are hydrogen or fluorine, characterized in that 1-substituted 2,3-difluorobenzenes are deprotonated in the 4-position using an organometallic reagent and optionally reacted with an electrophile.

The invention also relates to compounds of the formula I

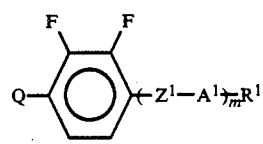

wherein
Q is

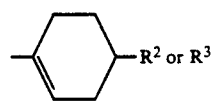

$R^2$ is H or an alkyl or alkenyl radical each having 1 to 15 C atoms, wherein one or more non-adjacent $CH_2$ groups may be replaced by 0 atoms, $R^3$ is M, F, Cl, Br, I, —CN, —$CF_3$, —$OR^4$, —$SR^4$, —$COR^4$, —CO—$OR^4$ or —O—$COR^4$, M is Li, Na or K, $R^4$ is H or an alkyl radical having 1 to 12 C atoms, is —$OCH_2$—, —$CH_2O$—, —$CH_2CH_2$—, —CH=CH—, —C≡C— or a single bond, $A^1$ is in each case independently a
 a) 1,4-cyclohexylene radical, wherein one or two non-adjacent $CH_2$ groups may be replaced by 0 atoms,
 b) 1,4-phenylene radical, wherein one or more CH groups may be replaced by N,
 c) radical from the group comprising 1,4-cyclohexenylene, piperidine-1,4-diyl, bicyclo(2,2,2)-octylene, naphthalene-2,6-diyl, decahydronaphthalene 2,6-diyl or 1,2,3,4-tetrahydronaphthalene, where the radical b) may be monosubstituted or disubstituted by F, Cl and/or —$CH_3$, m is 0, 1, 2 or 3, $R^1$ is an alkyl, perfluoroalkyl or alkenyl radical each having 1-15 C atoms, wherein one or more nonadjacent $CH_2$ or $CF_2$ groups may be replaced by O and/or S atoms, $R^1$ in the cases
 a) m equal to 0 may also be F, Cl or Br,
 b) m equal to 0 and Q equal to -CN may also be -OH,
 c) m equal to 0 and Q equal to M may also be M and
 d) m unequal to 0 may also be H with the proviso that Q and $R^1$ may not simultaneously be radicals selected from the group comprising F, Cl, Br, $CF_3$ and —OH, where in compounds in which all $A^1$ are radicals selected from the group comprising 1,4-phenylene which is unsubstituted or monosubstituted or disubstituted by F, at least one $Z^1$ is —$OCH_2$—, —$CH_2O$—, $CH_2CH_2$—, —CH=CH— or —C≡C—, and their reactive derivatives.

The invention furthermore relates to a process for the preparation of compounds of the formula I, characterized in that compounds which otherwise correspond to formula I, but in which Q is H, are deprotonated in the 4-position using an organometallic reagent and optionally reacted further with an electrophile, such as halogen (if desired with subsequent substitution of the halogen atom by —CN), ethylene oxide, a peroxide, disulfide or sulfur (if desired with subsequent etheri-fication or esterification), a reactive carbonyl compound or carbon dioxide (if desired with subsequent esterification or dehydration).

The invention finally relates to the use of compounds of the formula I as intermediates for the synthesis of liquid crystalline compounds.

For the sake of simplicity, in the following Ao

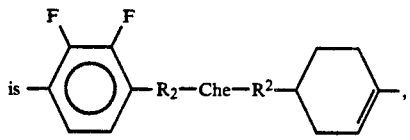

a, b and c are the radicals defined in formula I for $A^1$ under a, b and c, Nap is naphthalene-2,6-diyl, Pip is piperidine-1,4-diyl, Che is cyclohexenylene and BCO is bicyclo(2.2.2)octylene.

The compounds of the formula I accordingly include compounds of the sub-formulae Ia to Ih

| | |
|---|---|
| $R^3$—A°—$R^1$ | Ia |
| $R^2$—Che-A°—$R^1$ | Ib |
| $R^3$—A°—$Z^1$—$A^1$—$R^1$ | Ic |
| $R^2$—Che—A°—$Z^1$—$A^1$—$R^1$ | Id |
| $R^3$—A°—$Z^1$—$A^1$—$Z^1$—$A^1$—$R^1$ | Ie |
| $R^2$—Che-A°—$Z^1$—$A^1$—$Z^1$—$A^1$—$R^1$ | If |
| $R^3$—A°—$Z^1$—$A^1$—$Z^1$—$A^1$—$Z^1$—$A^1$—$R^1$ | Ig |
| $R^2$—Che—A°—$Z^1$—$A^1$—$Z^1$—$A^1$—$Z^1$—$A^1$—$R^1$ | IH |

Amongst these, those of the sub-formulae Ia to If are preferred.

The preferred compounds of the sub-formula Ic include those of the sub-formulae Ic1 to Ic6

| | |
|---|---|
| $R^3$—A°—$Z^1$—a—$R^1$ | Ic1 |
| $R^3$—A°—$Z^1$—b—$R^1$ | Ic2 |
| $R^3$—A°—$Z^1$—Nap—$R^1$ | Ic3 |
| $R^3$—A°—$Z^1$—Pip—$R^1$ | Ic4 |
| $R^3$—A°—$Z^1$—BCO—$R^1$ | Ic5 |
| $R^3$—A°—$Z^1$—Che—$R^1$ | Ic6 |

Amongst these, those of the sub-formulae Ic1, Ic2, Ic3. Ic5 and Ic6 are particularly preferred.

The preferred compounds of the sub-formula Id include those of the sub-formulae Id1 to Id6

| | |
|---|---|
| $R^2$—Che—A°—$Z^1$—a—$R^1$ | Id1 |
| $R^2$—Che—A°—$Z^1$—b—$R^1$ | Id2 |
| $R^2$—Che—A°—$Z^1$—Nap—$R^1$ | Id3 |
| $R^2$—Che—A°—$Z^1$—Pip—$R^1$ | Id4 |
| $R^2$—Che—A°—$Z^1$—BCO—$R^1$ | Id5 |
| $R^2$—Che—A°—$Z^1$—Che—$R^1$ | Id6 |

Amongst these, those of the sub-formulae Id1, Id2, Id3, Id5 and Id6 are particularly preferred.

The preferred compounds of the sub-formula Ie include those of the sub-formulae Ie1 to Ie8

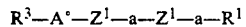  Ie1

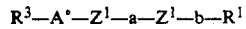  Ie2

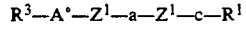  Ie3

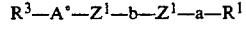  Ie4

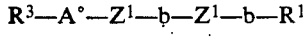  Ie5

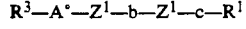  Ie6

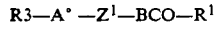  Ie6

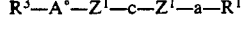  Ie7

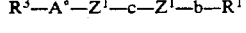  Ie8

Amongst these, those of the sub-formulae Ie1, Le2, Ie4, Ie5, Ie7 and Ie8 are particularly preferred.

The preferred compounds of the sub-formula If include those of the sub-formulae If1 to If8

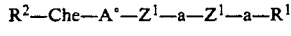  If1

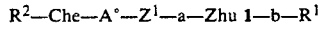  If2

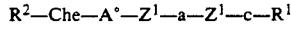  If3

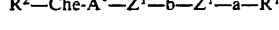  If4

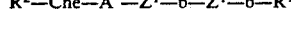  If5

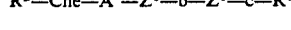  If6

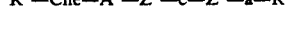  If7

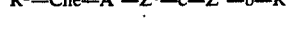  If8

Amongst these, those of the sub-formulae If1, If2, If4, If5, If7 and If8 are particularly preferred.

In the compounds of the formulae mentioned above and below, $R^1$ and $R^2$ are in each case independently of one another preferably an alkyl, alkenyl, alkoxy or an oxaalkyl radical each having 1 to 12 C atoms, and $R^1$ is also a perfluoroalkyl radical having 1 to 12 C atoms.

If $R^1$ and/or $R^2$ are alkyl radicals and/or alkoxy radicals, these can be linear or branched. Preferably, they are linear and consequently are preferably methyl, ethyl, propyl, butyl, pentyl, hexyl, heptyl, methoxy, ethoxy, propoxy, butoxy, pentoxy, hexoxy or heptoxy, and further octyl, nonyl, decyl, undecyl, dodecyl, octoxy, nonoxy, decoxy or undecoxy.

Oxaalkyl is preferably linear 2-oxapropyl (=methoxymethyl), 2-(=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 6- or 7-oxaoctyl, 2-, 3-, 4-, 5-, or 2-, 3-, 4-, 5-, 6-, 7-, 8- or 9-oxadecyl.

As a rule, branched groups of this type contain not more than one chain branching. Preferably branched radicals $R^1$ and $R^2$ are isopropyl, 2-butyl (=1-methylpropyl, isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 2-ethylhexoxy, 1-methylhexoxy or 1-methylheptoxy.

If $R^1$ and/or $R^2$ are alkenyl radicals, these can be linear or branched. Preferably they are linear and have 2 to 10 C atoms. They are consequently preferably vinyl, prop-1- or -2-enyl, but-1-, -2- or -3-enyl, pent-1-, -2-, -3- or -4-enyl, hex-1-, -2-, -3-, -4- or -5-enyl, hept-1-, -2-, -3-, -4-, -5- or -6-enyl, oct-1-, -2-, -3-, -4-, -5-, -6- or -7-enyl, non-1-, -2-, -3-, -4-, -5-, -6-, -7- or -8-enyl, or dec-1-, -2-, -3-, -4-, -5-, -6-, -7-, -8- or -9-enyl.

Furthermore, compounds are preferred in which m is equal to 0 and $R^1$ is equal to halogen such as F, Cl or Br. Furthermore, the compound is preferred in which Q is CN, m is O and $R^1$ is OH. Compounds are also particularly preferred in which $R^1$ is H, if m is different from zero.

$R^3$ is preferably M, halogen, —CN, -CF$_3$, —OR$^4$, —COR$^4$, —CO—OR$^4$ or —O—COR$^4$ Li, K, F, Cl, Br, I, —CN, OR$^4$—COR$^4$ and —CO—OR$^4$ are particularly preferred.

M is preferably Li or K.

$R^4$ is preferably H or an alkyl radical having 1 to 10 C atoms, in particular H or an unbranched alkyl radical such as methyl, ethyl, propyl, butyl, pentyl, hexyl, heptyl, octyl, nonyl, decyl, undecyl or dodecyl.

$Z^1$ is preferably a single bond, —CH$_2$O—, —OCH$_2$—, —CH$_2$—CH$_2$— or CH=CH—, in particular a single bond, —CH$_2$CH$_2$—, —CH$_2$O— or —OCH$_2$—.

a is preferably a 1,4-cyclohexylene or 1,3-dioxane -2,5-diyl radical.

b is preferably a 1,4-phenylene, pyridine-2,5-diyl or pyrimidine-2,5-diyl monosubstituted by F, Cl, —CN or —CH$_3$, and also the positional isomers of pyridine and pyrimidine radicals. An unsubstituted or substituted 1,4-phenylene radical and an unsubstituted pyridine-2,5-diyl or pyrimidine-2,5-diyl radical are particularly preferred.

c is particularly preferably Che, Pip, Nap and BCO, in particular Che.

The compounds of the formula I preferably contain not more than one heterocyclic radical.

m is preferably 0, 1 or 2.

Those compounds of the sub-formulae in which the radicals $R^1$, $R^2$, $R^3$, $R^4$, $Z^1$, a, b and c have the preferred meanings indicated are particularly preferred.

Very particularly preferred compounds according to the invention of the sub-formula Ia are consequently those of the sub-formulae Ia1 to Ia7

  Ia1

$$Br-A^\circ-R^1 \quad \text{Ia2}$$

$$J-A^\circ-R^1 \quad \text{Ia3}$$

$$CN-A^\circ-R^1 \quad \text{Ia4}$$

$$HO-A^\circ-R^1 \quad \text{Ia5}$$

$$H-OC-A^\circ-R^1 \quad \text{Ia6}$$

$$HO-OC-A^\circ-R^1 \quad \text{Ia7}$$

wherein M is Li or K and $R^1$ is an alkyl, alkenyl or alkoxy radical having up to 12 C atoms.

The preparation of the compounds of the formula I, in which Q is M, is carried out by the process according to the invention by deprotonation of corresponding compounds of the formula I, in which Q, however, is H.

In this connection, organometallic reagents and base systems which contain such reagents are suitable.

Amongst the organometallic reagents, alkyl- or aryl-metal compounds or alkali metal amides are particularly suitable. The base systems additionally contain an activator, preferably complexing agents such as amines or amides, that is, for example, hexamethylphosphoric triamide (HMPT), tetramethylethylenediamine (TMEDA) or N,N-dimethylpropyleneurea (DMPU) or metal exchange reagents such as, for example, potassium tert.-butoxide (KOT).

The reaction is carried out in inert solvents or mixtures thereof such as ethers and/or hydrocarbons at low temperatures, in general below −50° C., under protective gas. By reaction of the organometallic compounds resulting in this way with an electrophile, compounds of the formula I having substituents unequal to M in the 4-position are accessible. The reaction conditions are known for the reactions mentioned and can be taken from the standard works of preparative organic chemistry, for example HOUBEN-WEYL, Methoden der Organischen Chemie (Methods of Organic Chemistry), Georg-Thieme-Verlag, Stuttgart or ORGANIC SYNTHESES, J. Wiley, New York - London - Sydney. In this way, use can also be made of variants which are known per se but which are not mentioned in more detail here.

Reaction with electrophiles such as, for example, bromine, cyanogen bromide, tert. butyl hypobromite or chlorite, iodine or diiodomethane leads to compounds of the formula I in which Q is halogen such as Cl, Br or I. Cyano compounds (Q=CN) may be prepared by reacting appropriate bromine or iodine compounds of the formula I with a metal cyanide such as $Cu_2(CN)_2$, for example in the presence or pyridine in an inert solvent such as dimethylformamide (DMF) or N-methyl-pyrrolidin-2-one.

Phenols of the formula I (Q=OH) may be prepared by oxidizing the appropriate organometallic compounds (Q=M) with nitrobenzene or reacting with oxygen (passing gaseous $O_2$ into the reaction solution) or a peroxide. A preferred peroxide is, for example, lithium tert.-butyl peroxide. Furthermore, the cleavage of phenol ethers with Lewis acids likewise gives phenols.

Thiols and thioethers may be prepared by reacting appropriate organometallic compounds (Q=M) with sulfur or a persulfide.

Carboxylic acids of the formula I (Q=COOH) may be prepared by reacting appropriate organometallic compounds (Q=M) with carbon dioxide, by passing dry, gaseous $CO_2$ into the reaction solution or adding dry ice to the solution. Ethers of the formula I (compare the definitions for $R^1$, $R^2$, $R^3$ or $Z^1$) may be prepared by etherifying appropriate hydroxy bonds (sic). In this way, the hydroxy compound is preferably first converted into a corresponding derivative, for example is converted by treating with NaH, $NaNH_2$, NaOH, KOH, $Na_2CO_3$ or $K_2CO_3$ into the corresponding alkali metal alkoxide or alkali metal phenoxide. This can then be reacted with the corresponding alkyl halide, sulfonate or dialkyl sulfonate, preferably in an inert solvent such as acetone, 1,2-dimethoxyethane, DMF or dimethyl sulfoxide or even an excess of aqueous or aqueous alcoholic NaOH or KOH at temperatures between about 20° and 100° C.

The nitriles can be obtained from the carboxylic acids by conversion into the amides and subsequent dehydration.

Esters of the formula I ($R^3$=—CO—$OR^4$, —O—$COR^4$) can be obtained by esterification of corresponding carboxylic acids (or their reactive derivatives) with alcohols (or their reactive derivatives).

The acid halides, above all the chlorides and bromides, and further the anhydrides, azides or esters, in particular alkyl esters having 1-4 C atoms in the alkyl group, are particularly suitable as reactive derivatives of the carboxylic acids mentioned.

Possible reactive derivatives of the alcohols are, in particular, the corresponding metal alkoxides, preferably of an alkali metal such as Na or K.

The esterification is advantageously carried out in the presence of an inert solvent. In particular, ethers such as diethyl ether, di-n-butyl ether, THF, dioxane or anisole, ketones such as acetone, butanone or cyclohexanone, amides such as DMF or hexamethylphosphoramide, hydrocarbons such as benzene, toluene or xylene, halogenated hydrocarbons such as tetrachloromethane, tetrachloroethylene or dichloromethane and sulphoxides such as dimethyl sulphoxide or sulpholane are very suitable. Solvents which are immiscible with water can at the same time advantageously be used for the removal by azeotropic distillation of the water formed in the esterification. Occasionally, an excess of an organic base, for example pyridine, quinoline or triethylamine, may also be used as the solvent for the esterification. The esterification can also be carried out in the absence of a solvent, for example by simply heating the components in the presence of sodium acetate. The reaction temperature is usually between −50° and +250°, preferably between −20° and +180° C. At these temperatures, the esterification reactions are as a rule complete after 15 minutes to 48 hours.

Esterifications taking place under mild conditions are particularly preferred. This can be achieved by reaction with suitable dehydrating agents such as, preferably, dicylohexylcarbodiimide in one of the inert solvents indicated.

In detail, the reaction conditions for the esterification depend substantially on the nature of the starting materials used. Thus, a free carboxylic acid is reacted with a free alcohol, as a rule in the presence of a strong acid, for example a mineral acid such as hydrochloric acid or sulfuric acid. A preferred reaction procedure is the reaction of an acid anhydride or, in particular, an acid chloride with an alcohol, preferably in a basic medium, alkali metal hydroxides such as sodium hydroxide or potassium hydroxide, alkali metal carbonates or hydrogen carbonates such as sodium carbonate, sodium hydrogen carbonate, potassium carbonate or potassium hydrogen carbonate, alkali metal acetates such as sodium acetate or potassium acetate, alkaline earth metal hydroxides such as calcium hydroxide or organic bases such as triethylamine, pyridine, lutidine, collidine or quinoline being particularly important as bases. An additional preferred embodiment of the esterification consists in first converting the alcohol into the sodium or potassium alkoxide, for example by treating with ethanolic sodium hydroxide solution or potassium hydroxide solution, isolating this and suspending together with sodium hydrogen carbonate or potassium carbonate with stirring in acetone or diethyl ether and adding a solution of the acid chloride or anhydride in diethyl ether, acetone or DMF to this suspension, preferably at temperatures between about −25° and +20° C.

Aldehydes of the formula I (Q=CHO) may be prepared by reaction of the corresponding organometallic compounds (Q=M) with N-formylamides, for example N-formylpiperidine or N-formylmorpholine. Additional possibilities for synthesis are the reduction of appropriate carboxylic acids or the oxidation of appropriate primary alcohols according to the standard methods of organic chemistry.

Nitriles of the formula I can also be obtained from the aldehydes by conversion into the oxime with subsequent dehydration, or by reaction of the aldehydes with hydroxylamine-O-sulfonic acid and subsequent thermal elimination of sulfuric acid.

Ketones of the formula I (Q=COR$^4$, R$^4$=H) can be prepared by reaction of the appropriate organometallic compounds (Q=M) with aldehydes and subsequent oxidation of the resulting alcohols.

Compounds of the formula I having Q=R$^2$—Che— can be synthesized by reaction of the corresponding compounds with Q=M with 4-substituted cyclohexanones and subsequent dehydration.

On the other hand, compounds of the formula I can be prepared by deprotoning 2,3-difluorobenzene derivatives which are substituted by Q in the 1-position in the 4-position and, if necessary, reacting further with an electrophile. Only a few of the substituents de-fined for Q are suitable for this on account of possible competition reactions, for example addition to the carbonyl group. F, OR$^4$ (R$^4$=H) and R$^2$—Che are particularly suitable for Q. Other electrophiles can also be employed, as is described in the following.

In order to prepare alkyl-linked compounds of the formula I (for example Z$^1$=—CH$_2$—CH$_2$—or m=0 and R$^1$=alkyl or oxaalkyl), the organometallic compounds can be reacted with appropriate alkyl halides, preferably bromides or iodides. Another synthetic route is, for example, the reaction of the organometallic compounds with aldehydes, subsequent dehydration and final reduction of the resulting double bond.

Compounds of the formula I, in which Z$^1$ is —CH═CH—or —C≡C—, can be synthesized in the way described above: no reduction of the double bond or oxidation of the double bond to the triple bond by addition of bromine and elimination of two equivalents of hydrogen bromide.

Compounds of the formula I, in which an aromatic system is linked directly to the difluorophenylene radical, can be prepared by first converting the organometallic compounds by metal-metal exchange into other, preferably organic, transition metal compounds and subsequently reacting under catalytic conditions with an aryl or heteroaryl halide. However, the transmetalated compounds are also accessible from the appropriate halides, for example iodides, by metal-halide exchange. Preferred transition metals are Ti, Zn, Cu, Zr, Ni and Pd, in particular Ti and Zn. In addition to the transition metals, Mg, Al and Si are also preferred. However, other compounds of the formula I whose synthesis is also described above can be prepared to increase the reaction selectivity of the coresponding transmetalated compounds.

For example, the lithium-2,3-difluorophenyl compounds are converted into zinc (compare DE OS 3,632,410) or titanium compounds (compare DE OS 3,736,489) for reaction with aromatic halogen compounds.

Ketones of the formula I can then be prepared, for example, from these transmetalated compounds by reaction with a carboxylic acid chloride under transition metal catalysis.

Another important class of substances are the 2,3-difluorophenylboronic acids and their esters. They can be prepared in analogy to A.M. Roe, Chem. Comm. 22, 582 (1965) and, for example, converted into phenol derivatives according to literature cited therein.

Compounds of the formula I, in which a 1,4-phenylene radical or a 1,4-cyclohexylene radical is directly linked to the difluorophenylene radical, can also be prepared by initially reacting the appropriate organometallic compounds with cyclohexanone or appropriate derivatives thereof, subsequently dehydrating (Z$^1$=single bond, A$^1$=cyclohexenylene) and subsequently oxidizing or reducing.

Dioxane derivatives of the formula I (A$^1$ is 1,4-cyclohexylene in which two CH$_2$ groups are replaced by 0 atoms) are preferably prepared by reaction of an appropriate aldehyde with an appropriate 1,3-diol (or one of its reactive derivatives), preferably in the presence of an inert solvent such as benzene of toluene and/or a catalyst, for example a strong acid such as sulfuric acid, benzene- or p-toluenesulfonic acid, at temperatures between about 20° and about 150°, preferably between 80° and 120°. Suitable reactive derivatives of the starting materials are primarily acetals. Compounds according to the invention in which a pyridine ring is directly linked to the 2,3-difluorophenylene radical can be prepared, for example, by coupling 2-bromopyridine derivatives with a 2,3-difluorophenyl metal compound, for example titanium, under transition metal catalysis.

Analogous pyrimidine compounds can be prepared from 1-cyano-2,3-difluorophenylene compounds by conversion into an imido ester and reaction with an appropriate dialdehyde acetal in the presence of ammonia.

The starting compounds for the preparation of compounds of the formula I are known in some cases, that is, for example, 1,2-difluoro-3-isopropylbenzene (M. Attina et al., Tetrahedrbn Lett. 23, 3525) and 2,3-difluorobenzyl alcohol (EP 10,879), or are novel in some cases. The novel compounds among them are those of the formula II

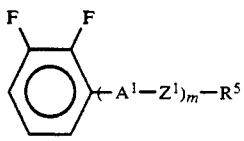

in which

A[1], Z[1] and m correspond to the definitions according to formula I and

R[5] in the case of m being unequal to O is H or an alkyl, perfluoroalkyl or alkenyl radical each having 1 to 15 C atoms, where one or more non-adjacent CH2 or CF2 groups in these radicals can be replaced by O and/or S atoms, excluding H in the case in which —(—A[1]—Z[1]—)m is a 1,4-phenylene radical which is unsubstituted or mono substituted by F, in the case of m being equal to O is an unbranched alkyl radical having 2 to 15 C atoms or a perfluorine or alkenyl radical having 2 to 15 C atoms, where one or more non-adjacent CH2 or CF2 groups in these radicals can be replaced by O and/or S atoms.

The invention likewise relates to them and they can, for their part, be prepared by metalating 2,3-difluoro-benzene, as described above, and reacting with an appropriate electrophile.

In this connection, the 1,4-dimetalated 2,3-difluorobenzenes may also be formed in varying amounts at the same time. Reaction with an electrophile then gives the corresponding symmetrical 1,4-disubstituted 2,3-difluorobenzenes therefrom.

Preferred compounds of the formula II according to the invention are

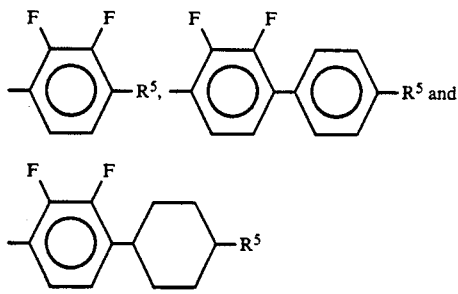

The following examples are intended to illustrate the invention in more detail, without limiting it.

Customary working up means: acidifying with dilute hydrochloric acid, separating off the organic phase, extracting with diethyl ether, dichloromethane or toluene, drying the organic phase, evaporating and purifying by chromatography, recrystallization and/or distillation.

The following abbreviations are used:
n-BuLi n-Butyllithium
t-BuOOH tert. Butyl peroxide
DDQ Dichlorodicyanobenzoquinone
DMPU N,N-dimethylpropyleneurea
m.p. Melting point
I Isotrope
C Crystalline
KOT Potassium tert.-butoxide
b.p. Boiling point
LiOOT Lithium tert.butyl peroxide
N Nematic
S Smectic
THF Tetrahydrofuran
TMEDA Tetramethylenediamine
pTsOH p-Toluenesulfonic acid

EXAMPLE 1

Metalation of difluorobenzene derivatives a) 0.1 mol of n-BuLi (1.5 M in hexane) is slowly added dropwise to a solution of 0.1 mol of difluorobenzene derivative cooled to −70° C. and the mixture is subsequently stirred for a further 6 hours at this temperature.

b) In modification of the directions for 1a), 0.1 mol of TMEDA is added to the solution of the difluorobenzene derivative and the mixture is subsequently stirred for 1 hour at −70° C.

c) 0.1 mol of n-BuLi (1.5 M in hexane) is added dropwise to a solution of 0.1 mol of the difluorobenzene derivative and 0.mol of KOT in 200 ml of THF cooled to −90° to −100° C. and the mixture is subsequently stirred for a further 5 minutes at this temperature.

EXAMPLE 2

Preparation of 3-pentyl-1,2-difluorobenzene 0.1 mol of pentyl bromide and subsequently 13 ml of DMPU are added dropwise to the solution of 1,2-difluorophenyl potassium in THF prepared according to 1c). After stirring below −85° C. for 60 minutes, the mixture is warmed in the course of 30 minutes to −40° C. and water is added at this temperature. The mixture is subsequently worked up as customary. b.p.30: 112° C.

The following are prepared analogously:
3-Methyl-1,2-difluorobenzene
3-Ethyl-1,2-difluorobenzene
3-Propyl-1,2-difluorobenzene, b.p.30: 72° C.
3-Butyl-1,2-difluorobenzene
3-Hexyl-1,2-difluorobenzene
3-Heptyl-1,2-difluorobenzene
3-Octyl-1,2-difluorobenzene, b.p.25: 145°
3-[2-(Cyclohexyl)-ethyl]-1,2-difluorobenzene
3-[2-(trans-4-Pentylcyclohexyl)-ethyl]-1,2-difluorobenzene, b.p.0.5: 135° C.

EXAMPLE 3

Preparation of 4-pentyl-2,3-difluoro-iodobenzene

3-Pentyl-1,2-difluorobenzene is metalated according to 1a) or 1b). A solution of 0.1 mol of iodine in 100 ml of diethyl ether is added slowly at −70° C. The mixture is subsequently stirred for a further hour at −70° C. and warmed to 0° C., and water is added to the solution. After washing with sodium hydrogen sulfite solution and dilute sodium hydroxide solution the mixture is worked up as customary.

The following are prepared analogously:
4-Methyl-2,3-difluoro-iodobenzene
4-Ethyl-2,3-difluoro-iodobenzene
4-Propyl-2,3-difluoro-iodobenzene
4-Hexyl-2,3-difluoro-iodobenzene
4-Heptyl-2,3-difluoro-iodobenzene
4-Octyl-2,3-difluoro-iodobenzene.

EXAMPLE 4

Preparation of 4-propyl-2,3-difluorobenzoic acid

3-Propyl-1,2-difluorobenzene (obtainable according to Example 2) is metalated as described in 1c). 20 g of dry ice are added slowly at −70° C. The mixture is subsequently warmed to −20° C. Customary working up gives colourless crystals, m.p. 148° C.

The following are prepared analogously:
4-Methyl-2,3-difluorobenzoic acid
4-Butyl-2,3-difluorobenzoic acid
4-Pentyl-2,3-difluorobenzoic acid
4-Heptyl-2,3-difluorobenzoic acid
4-Methoxy-2,3-difluorobenzoic acid
4-Ethoxy-2,3-difluorobenzoic acid
4-Butoxy-2,3-difluorobenzoic acid
4-Pentoxy-2,3-difluorobenzoic acid
4-Heptoxy-2,3-difluorobenzoic acid
4-Octoxy-2,3-difluorobenzoic acid, m.p.: 105° C.
4-(4-Methylcyclohexenyl)-2,3-difluorobenzoic acid
4-(4-Ethylcyclohexenyl)-2,3-difluorobenzoic acid
4-(4-Propylcyclohexenyl)-2,3-difluorobenzoic acid
4-(4-Pentylcyclohexenyl)-2,3-difluorobenzoic acid
4-(4-Heptylcyclohexenyl)-2,3-difluorobenzoic acid
4-(4-Methylphenyl)-2,3-difluorobenzoic acid
4-(4-Ethylphenyl)-2,3-difluorobenzoic acid
4-(4-Propylphenyl)-2,3-difluorobenzoic acid
4-(4-Pentylphenyl)-2,3-difluorobenzoic acid
4-(4-Heptylphenyl)-2,3-difluorobenzoic acid
4-(4-Methoxyphenyl)-2,3-difluorobenzoic acid
4-(4-Propoxyphenyl)-2,3-difluorobenzoic acid
4- 4-(4-Pentoxyphenyl)-2,3-difluorobenzoic acid.

EXAMPLE 5

Preparation of 4-ethoxy-2,3-difluorophenol 2,3-Difluoro-ethoxybenzene (obtainable by alkylation of 2,3-difluorophenol with potassium carbonate/ethyl iodide) is metalated according to 1b). 0.12 mol of LiOOT (solution in hexane/diethyl ether, prepared by adding dropwise 0.12 mol of n-BuLi (1.5 M in hexane) to a solution of 0.12 mol of t-BuOOH in 100 ml of diethyl ether at −5° to 0° C.) at −60° to −65° C. is added dropwise at this temperature. After stirring for 30 minutes at −60° C., the mixture is warmed to room temperature in the course of 2 hours. After customary working up (recrystallization from petroleum ether), colourless crystals are obtained, m.p. 73° C.

The following are prepared analogously:
4-Methyl-2,3-difluorophenol
4-Ethyl-2,3-difluorophenol
4-Propyl-2,3-difluorophenol
4-Butyl-2,3-difluorophenol
4-Pentyl-2,3-difluorophenol, b.p.0.5: 77° C.
4-Hexyl-2,3-difluorophenol
4-Octyl-2,3-difluorophenol
4-Nonyl-2,3-difluorophenol
4-Decyl-2,3-difluorophenol
4-Heptyl-2,3-difluorophenol
4- 4-Methoxy-2,3-difluorophenol
4-Propoxy-2,3-difluorophenol
4-Butoxy-2,3-difluorophenol
4-Pentoxy-2,3-difluorophenol
4-Hexoxy-2,3-difluorophenol
4-Heptoxy-2,3-difluorophenol
4-Octoxy-2,3-difluorophenol
4-Nonoxy-2,3-difluorophenol
4-Decoxy-2,3-difluorophenol
4-(4-Methylcyclohexenyl)-2,3-difluorophenol
4-(4-Ethylcyclohexenyl)-2,3-difluorophenol
4-(4-Propylcyclohexenyl)-2,3-difluorophenol
4-(4-Pentylcyclohexenyl)-2,3-difluorophenol
4-(4-Heptylcyclohexenyl)-2,3-difluorophenol
-(4-Methylphenyl)-2,3-difluorophenol
4-(4-Ethylphenyl)-2,3-difluorophenol
4-(4-Propylphenyl)-2,3-difluorophenol
4-(4-Pentylphenyl)-2,3-difluorophenol
4-(4-Heptylphenyl)-2,3-difluorophenol
4-(4-Methoxyphenyl)-2,3-difluorophenol
4-(4-Propoxyphenyl)-2,3-difluorophenol
4-(4-Pentoxyphenyl)-2,3-difluorophenol
44-[3-(2-trans-4-pentylcyclohexyl)-ethyl]-2,3-difluorophenol, m.p.: 61° C.

EXAMPLE 6

Preparation of 3-[4-(4-propylphenyl)-cyclohexenyl]-1,2-difluorobenzene

A solution of 0.1 mol of 4-(4-propylphenyl) cyclohexanone in 50 ml of THF is added dropwise at −70° C. to the solution of 1,2-difluorophenyllithium in THF/hexane prepared according to 1a). The mixture is then warmed to room temperature with stirring in the course of 2 hours. After customary working up, the residue is heated to boiling for 4 hours in a water separator in 150 ml of toluene after the addition of 1 g of p-TsOH. After cooling the mixture is worked up as customary (recrystallization from 150 ml of methanol/ethanol 1:1).

The following are prepared analogously:
3-[4-(4-Methylphenyl)-cyclohexenyl]-1,2-difluorobenzene
3-[4-(4-Ethylphenyl)-cyclohexenyl]-1,2-difluorobenzene
3-[4-(4-Pentylphenyl)-cyclohexenyl]-1,2-difluorobenzene
3-[4-(4-Hexylphenyl)-cyclohexenyl]-1,2-difluorobenzene
3-[4-(4-Heptylphenyl)-cyclohexenyl]-1,2-difluorobenzene
3-[4-(4-Methoxyphenyl)-cyclohexenyl]-1,2-difluorobenzene
3-[4-(4-Ethoxyphenyl)-cyclohexenyl]-1,2-difluorobenzene
3-[4-(4-Propoxyphenyl)-cyclohexenyl]-1,2-difluorobenzene
3-[4-(4-Pentoxyphenyl)-cyclohexenyl]-1,2-difluorobenzene
3-[4-(4-Heptoxyphenyl)-cyclohexenyl]-1,2-difluorobenzene
31,4-Di-(4-propylcyclohexenyl)-2,3-difluorobenzene
31,4-Di-(4-pentylcyclohexenyl)-2,3-difluorobenzene
3-(4-Methylcyclohexenyl)-1,2-difluorobenzene
3-(4-Ethylcyclohexenyl)-1,2-difluorobenzene
3-(4-Propylcyclohexenyl)-1,2-difluorobenzene, b.p.0.5: 91oC
3-(4-Pentylcyclohexenyl)-1,2-difluorobenzene, b.p.0.5: 123oC
3-(4-Heptylcyclohexenyl)-1,2-difluorobenzene
4-Methyl-1-(4-pentylcyclohexenyl)-2,3-difluorobenzene
4-Ethyl-1-(4-pentylcyclohexenyl)-2,3-difluorobenzene
4-Propyl-1-(4-pentylcyclohexenyl)-2,3-difluorobenzene
4-Pentyl-1-(4-pentylcyclohexenyl)-2,3-difluorobenzene
4-Heptyl-1-(4-pentylcyclohexenyl)-2,3-difluorobenzene
4-Methoxy-1-(4-pentylcyclohexenyl)-2,3-difluorobenzene
4-Ethoxy-1-(4-pentylcyclohexenyl)-2,3-difluorobenzene
4-Propoxy-1-(4-pentylcyclohexenyl)-2,3-difluorobenzene 4-Pentoxy-1-(4-pentylcyclohexenyl)-2,3-difluorobenzene 4-Heptoxy-1-(4-pentylcyclohexenyl)-2,3-difluorobenzene.

EXAMPLE 7

Preparation of 4-ethoxy-2,3-difluorobenzaldehyde

A solution of 0.1 mol of N-formylpiperidine in 10 ml of THF is added dropwise at −60° C. to the solution of 4-ethoxy-2,3-difluorophenyllithium in THF/hexane prepared according to 1b). The mixture is then warmed to −20° C. in the course of 1 hour. Customary working up (recrystallization from petroleum ether (boiling range 40°-60° C.) gives colourless crystals, m.p. 70° C.

The following are prepared analogously:
4-Methoxy-2,3-difluorobenzaldehyde
4-Propoxy-2,3-difluorobenzaldehyde
4-Pentoxy-2,3-difluorobenzaldehyde
4-Heptoxy-2,3-difluorobenzaldehyde
4-Methyl-2,3-difluorobenzaldehyde
4-Ethyl-2,3-difluorobenzaldehyde
4-Propyl-2,3-difluorobenzaldehyde
4-Pentyl-2,3-difluorobenzaldehyde
4- 10 4-Heptyl-2,3-difluorobenzaldehyde.

EXAMPLE 8

Preparation of 4-ethoxy-2,3-difluorobenzonitrile

4-Ethoxy-2,3-difluorobenzaldehyde (obtainable according to Example 7) is reacted with hydroxylamine-O-sulfonic acid according to J. Streith and C. Fizet, Helv. Chim. Acta 59, 2796 (1976), m.p.: 45° C.

The following are prepared analogously:
4-Methoxy-2,3-difluorobenzonitrile
4-Propoxy-2,3-difluorobenzonitrile
4-Pentoxy-2,3-difluorobenzonitrile
4-Heptoxy-2,3-difluorobenzonitrile
4-methyl-2,3-difluorobenzonitrile
4-Ethyl-2,3-difluorobenzonitrile
4-Propyl-2,3-difluorobenzonitrile
4-Pentyl-2,3-difluorobenzonitrile
4-Heptyl-2,3-difluorobenzonitrile.

EXAMPLE 9

Preparation of 4-cyano-2,3-difluorophenol

A solution of 0.1 mol of 4-ethoxy-2,3-difluoro benzonitrile in 100 ml of toluene is slowly added dropwise at room temperature in the course of 30 minutes to a solution of 0.1 mol of aluminium(III) chloride in 100 ml of toluene. The mixture is subsequently heated to boiling for 5 hours and worked up as customary after cooling, m.p.: 145° C.

EXAMPLE 10

Preparation of 4-bromo-2,3-difluorobenzonitrile 0.1 mol of trimethylsilyl chloride is added dropwise to a solution of 1,2-difluorophenylpotassium prepared according to 1c), the mixture is then metalated, in turn, according to 1c) and, as described in Example 7, converted into the aldehyde at −70° C. The conversion into the nitrile is carried out according to Example 8. The exchange of the silyl group for a Br atom is carried out by reaction with bromine.

EXAMPLE 11

Preparation of 3-propenyl-1,2-difluorobenzene

A solution of 0.13 mol of propionaldehyde in 30 ml of THF is added dropwise to the solution of 1,2-difluorophenyllithium in THF prepared according to 1b). The mixture is subsequently warmed to 0° C. and worked up as customary. The resulting crude product of the carbinol is dissolved in 80 ml of toluene and heated to boiling for 1 hour in a water separator with 1 g of p-TsOH. 0.2 ml of concentrated sulfuric acid are then added and the mixture is again heated for 1 hour, as above. It is then worked up as customary, b.p.30: 105° C.

The following are prepared analogously:
3-Butenyl-1,2-difluorobenzene
3-Pentenyl-1,2-difluorobenzene
3-Hexenyl-1,2-difluorobenzene
3-Heptenyl-1,2-difluorobenzene
3-Octenyl-1,2-difluorobenzene.

EXAMPLE 12

Preparation of 3-propyl-1,2-difluorobenzene

Hydrogen is introduced at room temperature until saturation into a solution of 0.13 mol of 3-propenyl-1,2-difluorobenzene (obtainable according to Example 11) in 100 ml of THF containing 5 g of suspended Pd/C. Customary working up is carried out after stirring for 3 hours, b.p.30 : 72° C.

The following are prepared analogously:
3-Butyl-1,2-difluorobenzene
3-Pentyl-1,2-difluorobenzene
3-Hexyl-1,2-difluorobenzene
3-Heptyl-1,2-difluorobenzene
3-Octyl-1,2-difluorobenzene.

EXAMPLE 13

Preparation of 3-(4-pentylphenyl)-1,2-difluorobenzene

A solution of 0.225 mol of 3-(4-pentylcyclohexenyl)-1,2-difluorobenzene (analogous to Example 6) and 0.55 mol of DDQ in 1.5 l of toluene is heated to boiling for 2 hours. The mixture is subsequently worked up as customary, b.p. 0.5: 125° C.

The following are prepared analogously:
3-(4-Methylphenyl)-1,2-difluorobenzene
3-(4-Ethylphenyl)-1,2-difluorobenzene
3-(4-Propylphenyl)-1,2-difluorobenzene

EXAMPLE 14

Preparation of 3-(4-methylcyclohexyl)-1,2-difluorobenzene 3-(4-Methylcyclohexenyl)-1,2-difluorobenzene (analogous to Example 6) is hydrogenated as described in Example 12.

The following are prepared analogously:
3-(4-Ethylcyclohexyl)-1,2-difluorobenzene
3-(4-Propylcyclohexyl)-1,2-difluorobenzene
3-(4-Pentylcyclohexyl)-1,2-difluorobenzene
3-(4-Heptylcyclohexyl)-1,2-difluorobenzene.

EXAMPLE 15

Preparation of 4-methyl-1-(5-methylpuridin-2-yl)-2,3-difluorobenzene 3-methyl-1,2-difluorobenzene is metalated according to 1a) (10 mmol). After the addition of 10 mmol of chlorotriisopropyl orthotitanate, the mixture is warmed to −20° C. and subsequently stirred for 15 minutes. 80 mg of tetrakis(triphenylphosphine)palladium(0) and 10 mmol of 2-bromo-5-methylpyridine are then added. Finally, the mixture is subsequently stirred for a further 18 hours at room temperature and worked up as customary.

The following are prepared analogously:
4-Ethyl-1-(5-methylpyridin-2-yl)-2,3-difluorobenzene
4-Propyl-1-(5-methylpyridin-2-yl)-2,3-difluorobenzene
4-Pentyl-1-(5-methylpyridin-2-yl)-2,3-difluorobenzene
4-Heptyl-1-(5-methylpyridin-2-yl)-2,3-difluorobenzene
4-Methoxy-1-(5-methylpyridin-2-yl)-2,3-difluorobenzene
4-Ethoxy-1-(5-methylpyridin-2-yl)-2,3-difluorobenzene, m.p.: 73° C.
4-Propoxy-1-(5-methylpyridin-2-yl)-2,3-difluorobenzene
4-Pentoxy-1-(5-methylpyridin-2-yl)-2,3-difluorobenzene
4-Heptoxy-1-(5-methylpyridin-2-yl)-2,3-difluorobenzene.

EXAMPLE 16

Preparation of trans-4-pentyl-cyclohexanecarboxylic acid 4-ethoxy-2,3-difluorophenoxide 10 mmol of trans-4-pentyl-cyclohexanecarbonyl chloride and 10 mmol of 4-ethoxy-2,3-difluorophenol are dissolved in 20 ml of dichloromethane. The mixture is stirred at room temperature for 6 hours after adding 15 mmol of pyridine and worked up as customary (recrystallization from methanol), C 48 N 62.5 I.

The following are prepared analogously:
trans-4-Pentyl-cyclohexanecarboxylic acid 4-methoxy-2,3-difluorophenoxide
trans-4-Pentyl-cyclohexanecarboxylic acid 4-propoxy-2,3-difluorophenoxide
trans-4-Pentyl-cyclohexanecarboxylic acid 4-pentoxy-2,3- difluorophenoxide
trans-4-Pentyl-cyclohexanecarboxylic acid 4-heptoxy-2,3-difluorophenoxide
trans-4-Pentyl-cyclohexanecarboxylic acid 4-octoxy-2,3- difluorophenoxide
trans-4-Pentyl-cyclohexanecarboxylic acid 4-methyl-2,3-difluorophenoxide
trans-4-Pentyl-cyclohexanecarboxylic acid 4-ethyl-2,3-difluorophenoxide
trans-4-Pentyl-cyclohexanecarboxylic acid 4-propyl-2,3-difluorophenoxide
trans-4-Pentyl-cyclohexanecarboxylic acid 4-pentyl-2,3-difluorophenoxide
trans-4-Pentyl-cyclohexanecarboxylic acid 4-heptyl-2,3-difluorophenoxide.

EXAMPLE 17

Preparation of 4'-heptyloxy-2,3-difluoro-biphenyl-4-carboxylic acid 0.1 mol of 2,3-difluoro-4'-heptyloxybiphenyl is metalated according to 1b). The mixture is stirred for 3 hours at −78° C. and the reaction mixture is then tipped in one swing onto 200 g of pulverized dry ice. The mixture is subsequently worked up as customary.

EXAMPLE 18

Preparation of 4-hydroxy-2,3-difluoro-4'-heptyloxybiphenyl 0.1 mol of 2,3-difluoro-4'-heptyloxybiphenyl (prepared by metalation of 2,3-difluorobenzene according to 1b) and reaction with heptyloxycyclohexane and also subsequent dehydration using toluene/p-TsOH in a water separator (analogous to Example 6) and aromatization using DDQ (analogous to Example 13), is metalated according to 1b) (stirring for 3 hours at −78° C.). Meanwhile, 70 ml of a 2 N solution of ethylmagnesium bromide in ether is added in the course of 30 minutes to a solution of 0.12 mol of tert.-butyl hydroperoxide in 50 ml of ether. The solution thus prepared is cautiously added dropwise to the solution of the metalated 2,3-difluoro-4'-heptyl-oxybiphenyl cooled to −78° C., then the mixture is allowed to warm to room temperature and is then stirred again for 2 hours. It is subsequently worked up as customary.

EXAMPLE 19

Preparation of 4-ethoxy-2,3-difluorophenol 0.02 mol of 2,3-difluoroethoxybenzene are metalated according to 1b. Subsequently, 0.02 mol of trimethyl borate are added dropwise at a temperature of about −55° to −60° C. during the course of 0.5 h. The resulting suspension is subsequently stirred for a further 0.5 h, the temperature climbing to about −20°. 1.5 ml of 98% acetic acid are added. After about 15 min, the mixture is cooled to about −35° and a solution of 30% $H_2O_2/H_2O$ (5 ml/2 ml) is added dropwise. After stirring for 2 h while slowly warming to room temperature, the organic phase is separated and the aqueous phase is extracted with methyl tert.butyl ether. Finally, the mixture is washed with saturated NaCl solution, dried and evaporated.

The following are prepared analogously:
4-Methyl-2,3-difluorophenol
4-Ethyl-2,3-difluorophenol
4-Propyl-2,3-difluorophenol
4-Butyl-2,3-difluorophenol
4-Pentyl-2,3-difluorophenol, b.p.0.5: 77° C.
4-Hexyl-2,3-difluorophenol
4-Octyl-2,3-difluorophenol
4-Nonyl-2,3-difluorophenol
4-Decyl-2,3-difluorophenol
4-Heptyl-2,3-difluorophenol
4-Methoxy-2,3-difluorophenol
4-Propoxy-2,3-difluorophenol
4-Butoxy-2,3-difluorophenol
4-Pentoxy-2,3-difluorophenol
4-Hexoxy-2,3-difluorophenol
4-Heptoxy-2,3-difluorophenol
4-Octoxy-2,3-difluorophenol
4-Nonoxy-2,3-difluorophenol
4-Decoxy-2,3-difluorophenol
4-(4-methylphenyl)-2,3-difluorophenol
4-(4-Ethylphenyl)-2,3-difluorophenol
4-(4-Propylphenyl)-2,3-difluorophenol
4-(4-Pentylphenyl)-2,3-difluorophenol
4-(4-Heptylphenyl)-2,3-difluorophenol
4-(4-Methoxyphenyl)-2,3-difluorophenol
4-(4-Propoxyphenyl)-2,3-difluorophenol
4-(4-Pentoxyphenyl)-2,3-difluorophenol.

EXAMPLE 20

Preparation of
3-(trans-4-pentylcyclohexyl)-methylenoxy
-1,2-difluorobenzene

A mixture of 2,3-difluorophenol (0.03 mol), (trans-4-pentylcyclohexyl)methyl iodide (0.035 mol), potassium carbonate (0.03 mol) and N-methylpyrrolidin-2-one (10 ml) is warmed to 100° C. for 24 hours. The mixture is subsequently worked up as customary. b.p.$_{0.5}$: 120° C.

EXAMPLE 21

Preparation of
4-octyloxy-1-[2-(trans-4-pentylcyclohexyl)-oxoethyl]-2,3-difluorobenzene 0.03 mol of 3-octyloxy-1,2-difluorobenzene are metalated according to 1a). Subsequently, a suspension of 0.03 mol of zinc bromide in 20 ml of THF is added slowly and the mixture is warmed to −10° C. 50 mg of Ni(Ph$_3$P)$_2$Cl$_2$ and a solution of 0.03 mol of 2-(trans-4-pentylcyclohexyl)-acetyl chloride in 20 ml of THF are then added. The mixture is warmed to room temperature, worked up as customary and recrystallized from methanol/ethanol (1:1), m.p.: 59° C., C 59 S$_A$ (55) I.

We claim:

1. A process for the preparation of a 1-substituted 2,3-difluorophenol of the formula

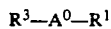

wherein
R$^3$ is OH;
A$^0$ is 2,3-difluoro-1,4-phenylene; and
R$^1$ is alkyl, perfluoroalkyl or alkenyl, in each case having 1-15 C atoms, wherein one or more non-adjacent CH$_2$ or CF$_2$ groups is optionally replaced by O; said process comprising:
deprotonating in the 4-position a 1-substituted 2,3-difluorobenzene at a temperature below about −50° C. using an organometallic reagent; and
reacting the resultant product with an electrophile, said electrophile being nitrobenzene, oxygen, or a peroxide.

2. A 2,3-difluorophenol compound according to the formula

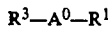

wherein
R$^3$ is OH;
A$^0$ is 2,3-difluoro-1,4-phenylene; and
R$^1$ is alkyl, perfluoroalkyl or alkenyl, in each case having 1-15 C atoms, wherein one or more non-adjacent CH$_2$ or CF$_2$ groups is optionally repalced by O;

3. A process according to claim 1, wherein deprotonation occurs within a reaction solution and said electrophile is gaseous oxygen which is passed itno said reaction solution.

4. A process according to claim 1, wherein said organometallic reagent is an alkyl metal compound, an aryl metal compound, or an alkyl metal amide.

5. A process according to claim 1, wherein said organometallic reagent contains the metal Li, Na or K.

6. A process according to claim 4, wherein said organometallic reagent contains the metal Li, Na or K.

7. A process according to claim 1, wherein said organometallic reagent is n-butyl lithium.

8. A process according to claim 1, wherein said electrophile is lithium tert.-butyl peroxide.

9. A process according to claim 1, wherien said organometallic reagent contains Li or K.

10. A process according to claim 1, wherein said organometallic reagent contains Li.

11. A process according to claim 1, wherein said electrophile is H$_2$O$_2$.

12. A process according to claim 1, wherein said substituted 2,3-difluorophenol is:
4-methyl-2,3-difluorophenol, 4-ethyl -2,3-difluorophenol, 4-propyl-2,3-difluorophenol, 4-butyl-2,3-difluorophenol, 4-pentyl-2,3-difluorophenol 4-hexyl-2,3-difluorophenol, 4-octyl-2,3-difluorophenol, 4-nonyl -2,3-difluorophenol, 4-decyl-2,3-difluorophenol, 4-heptyl-2,3-difluorophenol, 4-methoxy-2,3-difluorophenol, 4-propoxy-2,3-difluorophenol, 4-butoxy -2,3-difluorophenol, 4-pentoxy-2,3-difluorophenol, 4-hexoxy-2,3-difluoorphenol, 4-heptoxy-2,3-difluorophenol, 4-octoxy-2,3-difluorophenol, 4-nonoxy-2,3-difluorophenol, or 4-decoxy -2,3-difluorophenol.

13. A compound according to claim 2, wherein said substituted 2,3-difluorophenol is:
4-methyl-2,3-difluorophenol, 4-ethyl -2,3-difluorophenol, 4-propyl-2,3-difluorophenol 4-butyl-2,3-difluorophenol, 4-pentyl-2,3-difluorophenol, 4-hexyl -2,3-difluorophenol, 4-octyl-2,3-difluorophenol, 4-nonyl-2,3-difluorophenol, 4-decyl -2,3-difluorophenol, 4-heptyl-2,3-difluorophenol, 4-methoxy-2,3-difluorophenol, 4-propoxy -2,3-difluorophenol, 4-butoxy-2,3difluorophenol, 4-pentoxy-2,3-difluorophenol, 4-hexoxy -2,3-difluorophenol, 4-heptoxy-2,3-difluorophenol, 4-octoxy-2,3-difluorophenol, 4-nonoxy -2,3-difluorophenol, or 4-decoxy-2,3-difluorophenol.

14. A process according to claim 1, wherein said substituted 2,3-difluorophenol is 4-ethoxy -2,3-difluorophenol.

15. A compound according to claim 2, wherein said substituted 2,3-difluorophenol is 4-ethoxy -2,3-difluorophenol.

* * * * *